(12) United States Patent
Schneid

(10) Patent No.: US 8,048,084 B2
(45) Date of Patent: Nov. 1, 2011

(54) SURGICAL INSTRUMENT

(75) Inventor: Susanne Schneid, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 1379 days.

(21) Appl. No.: 11/221,249

(22) Filed: Sep. 7, 2005

(65) Prior Publication Data

US 2006/0058808 A1    Mar. 16, 2006

(30) Foreign Application Priority Data

Sep. 8, 2004 (DE) .......................... 10 2004 043 996

(51) Int. Cl.
*A61B 17/58* (2006.01)
(52) U.S. Cl. ...................... 606/99; 606/86 A; 623/17.15
(58) Field of Classification Search ................ 606/86 A, 606/86 B, 99; 623/17.11–17.16
See application file for complete search history.

(56) References Cited

U.S. PATENT DOCUMENTS

| | | | |
|---|---|---|---|
| 2,737,954 A | 3/1956 | Knapp | |
| 4,736,738 A | 4/1988 | Lipovsek | |
| 4,997,432 A * | 3/1991 | Keller | ........................ 623/17.11 |
| 5,122,130 A | 6/1992 | Keller | |
| 5,314,477 A | 5/1994 | Marnay | |
| 5,720,751 A * | 2/1998 | Jackson | ...................... 606/86 R |
| 5,741,253 A | 4/1998 | Michelson | |
| 5,782,830 A | 7/1998 | Farris | |
| 5,782,832 A * | 7/1998 | Larsen et al. | .............. 623/17.11 |
| 5,910,141 A | 6/1999 | Morrison | |
| 5,951,564 A | 9/1999 | Schroder | |
| 6,004,326 A | 12/1999 | Castro | |
| 6,033,438 A | 3/2000 | Bianchi | |
| 6,174,311 B1 | 1/2001 | Branch | |
| 6,197,033 B1 | 3/2001 | Haid, Jr. | |
| 6,267,763 B1 | 7/2001 | Castro | |
| 6,428,541 B1 | 8/2002 | Boyd | |
| 6,440,142 B1 * | 8/2002 | Ralph et al. | ..................... 606/99 |
| 6,524,312 B2 | 2/2003 | Landry | |
| 6,540,785 B1 | 4/2003 | Gill | |
| 6,582,437 B2 | 6/2003 | Dorchak | |

(Continued)

FOREIGN PATENT DOCUMENTS

DE            203 10 433 U1        7/2003

(Continued)

*Primary Examiner* — Eduardo C Robert
*Assistant Examiner* — Julianna N Harvey
(74) *Attorney, Agent, or Firm* — RatnerPrestia

(57) ABSTRACT

So that a surgical instrument for inserting an intervertebral implant into an intervertebral space between two adjacent vertebral bodies of two vertebrae of a human or animal spinal column, wherein the intervertebral implant comprises a first abutment element for abutment against one of the two adjacent vertebral bodies as well as a second abutment element directly or indirectly supported in an articulated manner on the first abutment element for abutment against the other of the two adjacent vertebral bodies, wherein the instrument comprises an elongate shank, which defines a longitudinal direction and on the distal end of which at least two abutment-element holding elements are provided for detachable connection to the first and the second abutment element, and a spacer element, which projects from the distal end of the shank in extension thereof and which, when the abutment elements are connected to the instrument, engages between the abutment elements and holds them a defined spacing apart from one another, may be improved in such a way that with it a plurality of different implants, in particular of differing sizes, is insertable through different approaches into the intervertebral space, it is proposed that the spacer element is supported movably relative to at least one of the two abutment-element holding elements.

35 Claims, 4 Drawing Sheets

U.S. PATENT DOCUMENTS

| | | |
|---|---|---|
| 6,599,291 B1 | 7/2003 | Foley |
| 6,635,062 B2 | 10/2003 | Ray, III |
| 6,648,895 B2 | 11/2003 | Burkus |
| 6,652,533 B2 | 11/2003 | O'Neil |
| 6,719,760 B2 | 4/2004 | Dorchak |
| 6,723,096 B1 | 4/2004 | Dorchak |
| 6,746,454 B2 | 6/2004 | Winterbottom |
| 6,755,841 B2 | 6/2004 | Fraser |
| 6,824,565 B2 | 11/2004 | Muhanna |
| 6,863,673 B2 * | 3/2005 | Gerbec et al. ............ 606/99 |
| 6,899,715 B1 | 5/2005 | Beaty |
| 6,916,323 B2 * | 7/2005 | Kitchens ............ 606/86 R |
| 6,929,647 B2 | 8/2005 | Cohen |
| 7,128,761 B2 * | 10/2006 | Kuras et al. ............ 623/17.15 |
| 7,169,153 B2 * | 1/2007 | Keller ............ 606/99 |
| 7,803,162 B2 * | 9/2010 | Marnay et al. ............ 606/99 |
| 2001/0016741 A1 | 8/2001 | Burkus |
| 2001/0031968 A1 | 10/2001 | Dorchak |
| 2002/0022847 A1 | 2/2002 | Ray, III |
| 2002/0058950 A1 | 5/2002 | Winterbottom et al. |
| 2002/0068936 A1 | 6/2002 | Burkus |
| 2003/0040752 A1 * | 2/2003 | Kitchens ............ 606/86 |
| 2003/0074005 A1 | 4/2003 | Roth |
| 2003/0083747 A1 | 5/2003 | Winterbottom |
| 2003/0135220 A1 | 7/2003 | Cauthen |
| 2003/0195520 A1 | 10/2003 | Boyd |
| 2003/0212404 A1 | 11/2003 | Dorchak |
| 2003/0216744 A1 | 11/2003 | Longhini |
| 2004/0024408 A1 | 2/2004 | Burkus |
| 2004/0097932 A1 | 5/2004 | Ray, III |
| 2004/0143331 A1 | 7/2004 | Errico |
| 2004/0148027 A1 | 7/2004 | Errico |
| 2004/0153158 A1 | 8/2004 | Errico |
| 2004/0158325 A1 | 8/2004 | Errico |
| 2004/0167534 A1 | 8/2004 | Errico |
| 2004/0172037 A1 | 9/2004 | Dorchak |
| 2004/0176775 A1 | 9/2004 | Burkus |
| 2004/0176843 A1 | 9/2004 | Zubok |
| 2004/0176852 A1 | 9/2004 | Zubok |
| 2004/0186576 A1 | 9/2004 | Biscup |
| 2004/0193272 A1 | 9/2004 | Zubok |
| 2004/0199168 A1 | 10/2004 | Bertagnoli |
| 2004/0220670 A1 * | 11/2004 | Eisermann et al. ............ 623/17.14 |
| 2005/0027300 A1 | 2/2005 | Hawkins |
| 2005/0033305 A1 | 2/2005 | Schultz |
| 2005/0038511 A1 | 2/2005 | Martz |
| 2005/0060035 A1 | 3/2005 | Errico |
| 2005/0143749 A1 | 6/2005 | Zalenski |
| 2005/0251146 A1 | 11/2005 | Martz |

FOREIGN PATENT DOCUMENTS

| | | |
|---|---|---|
| DE | 10 2004 043 995.8 | 9/2004 |
| EP | 0 333 990 B1 | 9/1989 |
| EP | 0 471 821 B1 | 2/1992 |
| WO | WO 01/19295 A1 | 9/1999 |

* cited by examiner

SURGICAL INSTRUMENT

The present disclosure relates to the subject matter disclosed in German patent application 10 2004 043 996.6 of Sep. 8, 2004 which is incorporated herein by reference in its entirety and for all purposes.

BACKGROUND OF THE INVENTION

The invention relates to a surgical instrument for inserting an intervertebral implant into an intervertebral space between two adjacent vertebral bodies of two vertebrae of a human or animal spinal column, wherein the intervertebral implant comprises a first abutment element for abutment against one of the two adjacent vertebral bodies as well as a second abutment element directly or indirectly supported in an articulated manner on the first abutment element for abutment against the other of the two adjacent vertebral bodies, wherein the instrument comprises an elongate shank, which defines a longitudinal direction and on the distal end of which at least two abutment-element holding elements are provided for detachable connection to the first and the second abutment element, and a spacer element, which projects from the distal end of the shank in extension thereof and which, when the abutment elements are connected to the instrument, engages between the abutment elements and holds them a defined spacing apart from one another.

Instruments of the initially described type are used to insert intervertebral implants with movable implant components, in particular to insert replacement intervertebral disks. In this case, a basic distinction is made between two types of instrument. On the one hand, there are instruments, with which first the abutment elements are disposed against the adjacent vertebral bodies and only in a next step is an articulated element inserted between the two abutment elements. With this procedure, spreading of the adjacent vertebral bodies is an absolute requirement. Known insertion instruments accordingly also have a spreading function. On the other hand, insertion instruments are known, with which an intervertebral implant may be inserted as a unit between adjacent vertebral bodies. Known insertion instruments are each individually adapted to the replacement intervertebral disk that is to be inserted.

SUMMARY OF THE INVENTION

It is an advantage of the present invention that with an instrument of the initially described type that is improved according to the invention a plurality of different implants, in particular of differing sizes, is insertable into an intervertebral space.

This is achieved in particular in that the spacer element is supported movably relative to at least one of the two abutment-element holding elements.

This development makes it possible to use the insertion instrument to hold intervertebral implants of differing size, in particular in different positions. By virtue of supporting the spacer element movably relative to at least one of the two abutment-element holding elements, the position of the spacer element may be adapted in a desired manner to the implant to be inserted in each case. In said case, it would in particular be conceivable for the spacer element to be rotated, displaced in a translatory manner within a plane of motion or displaced transversely of the plane of motion. It is therefore possible to act with the insertion instrument in different positions on the implant to be inserted and to move the spacer element into the position, in which the spacer element holds the abutment elements connected to the instrument a defined spacing apart from one another. Thus, intervertebral implants may be introduced in particular also through different approaches, i.e. from different directions, e.g. from an anterior or lateral direction, into the intervertebral space.

The spacer element is preferably supported movably transversely or substantially transversely of the longitudinal direction of the shank. It is therefore possible to act with the instrument not only centrally but also laterally on the intervertebral implant to be inserted, wherein owing to the transverse mobility of the spacer element in relation to the longitudinal direction a lateral offset in relation to a symmetrical basic position of the instrument is possible and the abutment elements connected to the instrument may be held in a desired manner a defined spacing apart from one another.

It is further advantageous when the spacer element is supported movably parallel or substantially parallel to the longitudinal direction of the shank. In this way, an unwanted tilting of the two abutment elements relative to one another may be prevented, namely in that the spacer element is moved substantially in such a way that both abutment elements are supported over a large area against the spacer element, in particular around an edge thereof, and so a tilting of the abutment elements relative to the spacer element, in particular around an edge thereof, is prevented.

It is particularly advantageous when the intervertebral implant comprises an articulated element disposed between the first and the second abutment element. In this way, a lordosis angle formed between the articular surfaces of the vertebral bodies delimiting the intervertebral space may be reconstructed in an optimum manner. It moreover allows an almost natural mobility of the two abutment elements relative to one another.

In an advantageous manner, the articulated element can be encompassed at least partially by the spacer element. This results in a particularly good support of the two abutment elements against the spacer element. It may therefore be ensured particularly well that the articulated element maintains a desired position, equally that the two abutment elements may be held a desired spacing apart from one another.

The construction of the instrument becomes particularly simple when the spacer element is of a substantially U-shaped design. This moreover allows it to be easily displaced relative to the two abutment elements.

It would in principle be conceivable for the spacer element to be of a semicircular design. The spacer element preferably comprises two limbs directed in distal direction parallel or substantially parallel to the longitudinal direction of the shank. This allows a position of the spacer element to be readjusted in a desired manner in a direction parallel to the longitudinal direction of the shank.

It is advantageous when a spacing between the two limbs is greater than a width of the articulated element and when the spacing between the two limbs corresponds at most to the width of the first and second abutment element. By virtue of this dimensioning it is ensured that the spacer element is introducible on either side of the articulated element between the two abutment elements and may hold the two abutment elements a desired spacing apart from one another.

A height of the spacer element is advantageously equal to or greater than a minimum possible spacing of the first abutment element from the second abutment element. This prevents forces, which act upon the two abutment elements during insertion of the implant, in the direction of the other abutment element from being able to lead to damage of the articulated element. If the height of the spacer element is slightly greater than a minimum possible spacing of the first abutment element from the second abutment element in a finally inserted position of the implant in the intervertebral space, then the implant may be inserted without contact between parts of the implant that lie adjacent to one another in the inserted position. In this way, damage to the implant during insertion is avoided even more effectively.

In order to prevent damage being caused to the implant during insertion by an unintentional movement of the spacer element relative to the two abutment elements, it is advantageous when the spacer element is securable in at least one transverse movement position, which is defined or movable in a defined manner, relative to the shank. This at least one transverse movement position may be so selected that it corresponds to one or more special coupling positions of the instrument on the implant, for example mid-centre or laterally offset coupling positions of the instrument on the implant.

It would in principle be conceivable for the spacer element to be supported pivotably relative to the shank. Such a support becomes particularly stable when the spacer element is supported displaceably relative to the shank.

The stability of the instrument and the precision and reproducibility of the setting of a specific position of the spacer element may be increased when a displacement guide is provided for the spacer element.

Two independent setting options for the spacer element may be realized when the spacer element is supported movably on a holding element and when the holding element is supported movably relative to the shank in longitudinal direction thereof. This allows the spacer element to be displaced for example in a translatory manner in one plane. It would however also be conceivable to rotate the spacer element relative to the holding element.

It is advantageous when at least two corresponding locking elements are provided for locking a relative position of the spacer element and the holding element in a locking position, in which the spacer element and the holding element are secured such that they are immovable relative to one another or movable in a defined manner, and when the spacer element carries a first and the holding element carries a second of the at least two locking elements. In this way, a relative position of the spacer element and the holding element may be secured in a particularly simple manner. A position movable in a defined manner may be defined for example by means of an elongate indentation or opening, in which a projection is guided between two defined stops.

The construction of the instrument becomes particularly simple when the one first locking element is a locking receiver and the one second locking element is a locking projection.

In particular when a transverse movement of the spacer element relative to longitudinal direction of the shank is to be secured, it is advantageous when the locking projection is supported movably parallel or substantially parallel to the longitudinal direction of the shank.

So that the at least two locking elements may be secured in the locking position against unintentional detachment, it is advantageous when the locking projection is supported spring-biased in the direction of the locking receiver. The locking projection may then engage in a spring-actuated manner into the locking receiver.

The locking position may be secured in a particularly simple manner against unintentional detachment when the one of the at least two locking elements is designed in the form of a spherical thrust piece. The locking receiver is then preferably of a corresponding design to the spherical thrust piece, being designed in particular in the form of a hemispherical indentation or a corresponding elongate groove with lateral stops, which are used to limit the movement, for the spherical thrust piece.

In order to ensure that the spacer element may be secured in at least two locking positions, it is advantageous when the holding element and/or the spacer element carries at least two locking elements. These may be, for example, two locking receivers or two locking projections that can be brought in each case into engagement with a further locking element.

A connection of the spacer element to the remaining instrument becomes particularly stable when the displacement guide is formed by an opening, which is disposed transversely of the longitudinal direction of the shank and is at least partially open in the direction of the spacer element. In this way, it is possible to form, for example, a slot guide for the spacer element.

The intervertebral implant may be connected to the instrument in a simple manner when a stop device is provided for limiting a movement of the abutment-element holding elements away from another. In this way, in particular an unintentional detachment of an articulated element inserted loosely between the two abutment elements is additionally prevented. In said case, it may be advantageous when the stop device is variable, i.e. a maximum spacing between the abutment-element holding elements is definable in dependence upon the setting of the stop device. Thus, for example, abutment-element holding elements that are supported resiliently relative to one another may be moved away from one another to a differing extent, depending on how the stop device is set.

The construction of the stop device becomes particularly simple when the stop device comprises a stop element that encompasses both abutment-element holding elements in each case at least partially.

It would in principle be conceivable for the stop element to be of a clamp-like design. The construction of the instrument is however further simplified when the stop element is a sleeve supported movably in longitudinal direction of the shank. The sleeve may be displaced in longitudinal direction of the shank or moved in the manner of a screw, in which case a distal end of the sleeve is displaced in longitudinal direction of the shank.

According to a preferred embodiment of the invention it may be provided that the stop device comprises at least one slide surface for a distal end of the sleeve, that the slide surface is formed on one of the two abutment-element holding elements or adjacent thereto on the shank, and that the slide surface in distal direction relative to the longitudinal direction of the shank is inclined away from a longitudinal axis of the shank. This development allows the abutment-element holding elements to be moved towards one another by moving the sleeve in distal direction. Conversely, the abutment-element holding elements biased towards one another may spring away from one another when the sleeve is moved back in proximal direction.

The instrument may be connected to the intervertebral implant in a simple manner when the abutment-element holding element carries at least one holding pin, which projects in distal direction parallel to the longitudinal direction of the shank and is of a corresponding design to at least one holding-pin receiver of the abutment element. By moving the instrument parallel to the longitudinal direction of the shank towards the intervertebral implant a connection may be established. It is in particular advantageous when the abutment element has more than one holding-pin receiver so that the instrument is connectable in various positions to the intervertebral implant and may also be coupled, for example, laterally to the implant.

According to a further preferred embodiment of the invention it may be provided that at least the distal end of the instrument is of a forked design comprising two fork ends, which are movable relative to one another, and that the two fork ends form or carry the abutment-element holding elements. In particular, the fork ends may be spring-biased in such a way that they may be pressed together only after loading with a force.

A mechanical drive unit is advantageously provided for moving the spacer element in longitudinal direction of the shank. A user of the instrument may then bring about a movement of the spacer element in longitudinal direction of the shank by loading the drive unit with a force. In particular, it would be possible to provide an indicating device for indicating a relative position of the spacer element relative to the shank.

The mechanical drive unit may be realized in a particularly simple manner when it comprises a threaded spindle extending in longitudinal direction of the shank as well as a rotary knob supported on the shank and coupled to the threaded spindle. This allows the threaded spindle to be displaced in longitudinal direction of the shank through rotation of the rotary knob.

It is advantageous when the intervertebral implant is a replacement intervertebral disk.

It is advantageous when the articulated element and one of the two abutment elements are of an integral construction. This allows the number of parts of the implant to be minimized to two.

The articulated element and at least one of the two abutment elements preferably lie loosely adjacent to one another, in particular in the insertion position and also in an implanted position. In this way, it is possible to dispense with additional connection elements for connecting the abutment element to the articulated element and therefore reduce an overall height of the implant as a whole.

In order to guarantee that the implant parts are held together particularly well, it is advantageous when the articulated element and at least one of the two abutment elements are non-positively and/or positively connected to one another.

In order also to be able to vary distances between the abutment elements, it is advantageous when the spacer element is held in a detachably connectable manner on the instrument. Thus, for example, one or more further spacer elements may be provided, which may be connected to the instrument depending on the type and size of the implant to be inserted. Preferably, a set of different spacer elements is provided.

According to the invention the initially stated object is further achieved in that one of the previously described instruments is used to insert an intervertebral implant into an intervertebral space between two adjacent vertebral bodies of two vertebrae of a human or animal spinal column, wherein the intervertebral implant comprises a first abutment element for abutment against one of the two adjacent vertebral bodies as well as a second abutment element directly or indirectly supported in an articulated manner on the first abutment element for abutment against the other of the two adjacent vertebral bodies.

According to the invention the initially stated object is further achieved by an implant system comprising an intervertebral implant for insertion into an intervertebral space between two adjacent vertebral bodies of two vertebrae of a human or animal spinal column as well as an insertion instrument for inserting the intervertebral implant into the intervertebral space, wherein the intervertebral implant comprises a first abutment element for abutment against one of the two adjacent vertebral bodies as well as a second abutment element directly or indirectly supported in an articulated manner on the first abutment element for abutment against the other of the two adjacent vertebral bodies, wherein the insertion instrument is one of the previously described surgical instruments.

BRIEF DESCRIPTION OF THE DRAWINGS

A detailed explanation is provided by the following description in connection with the drawings. The drawings show.

DETAILED DESCRIPTION OF THE INVENTION

Figure 1:
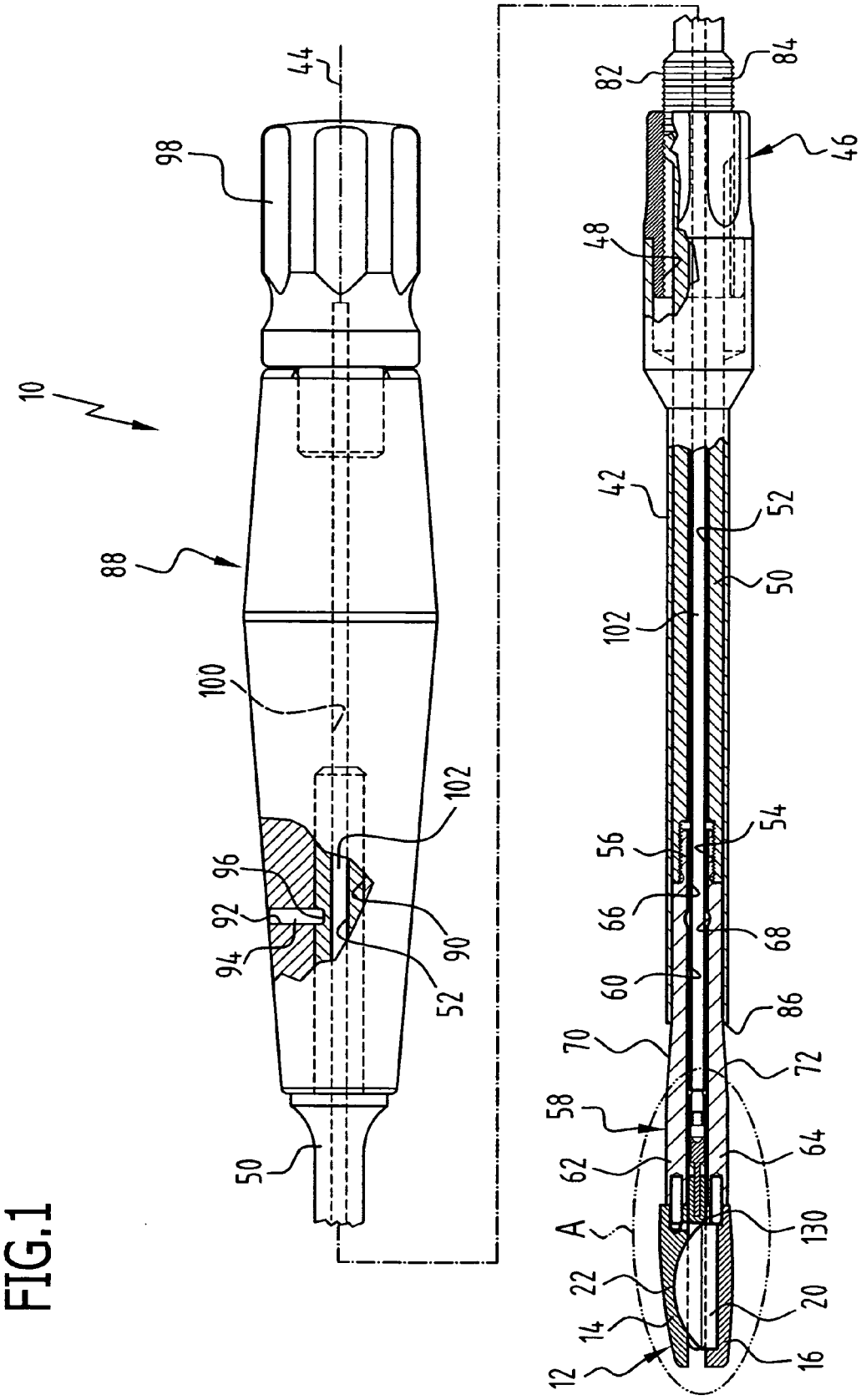
FIG. 1: a partially broken-through and part-sectional side view of an insertion instrument.
Figure 2:
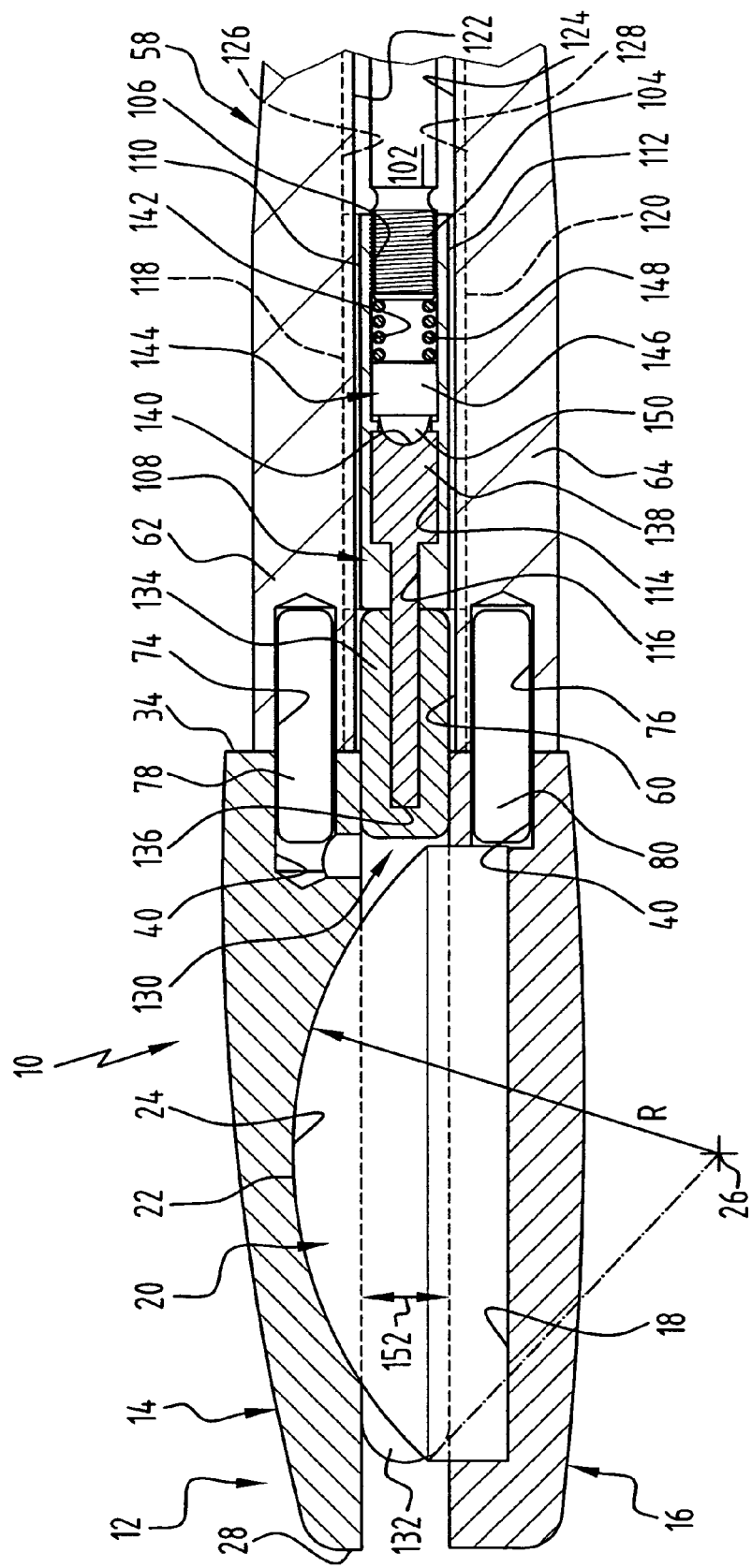
FIG. 2: an enlarged view of the region A in FIG. 1.
Figure 3:
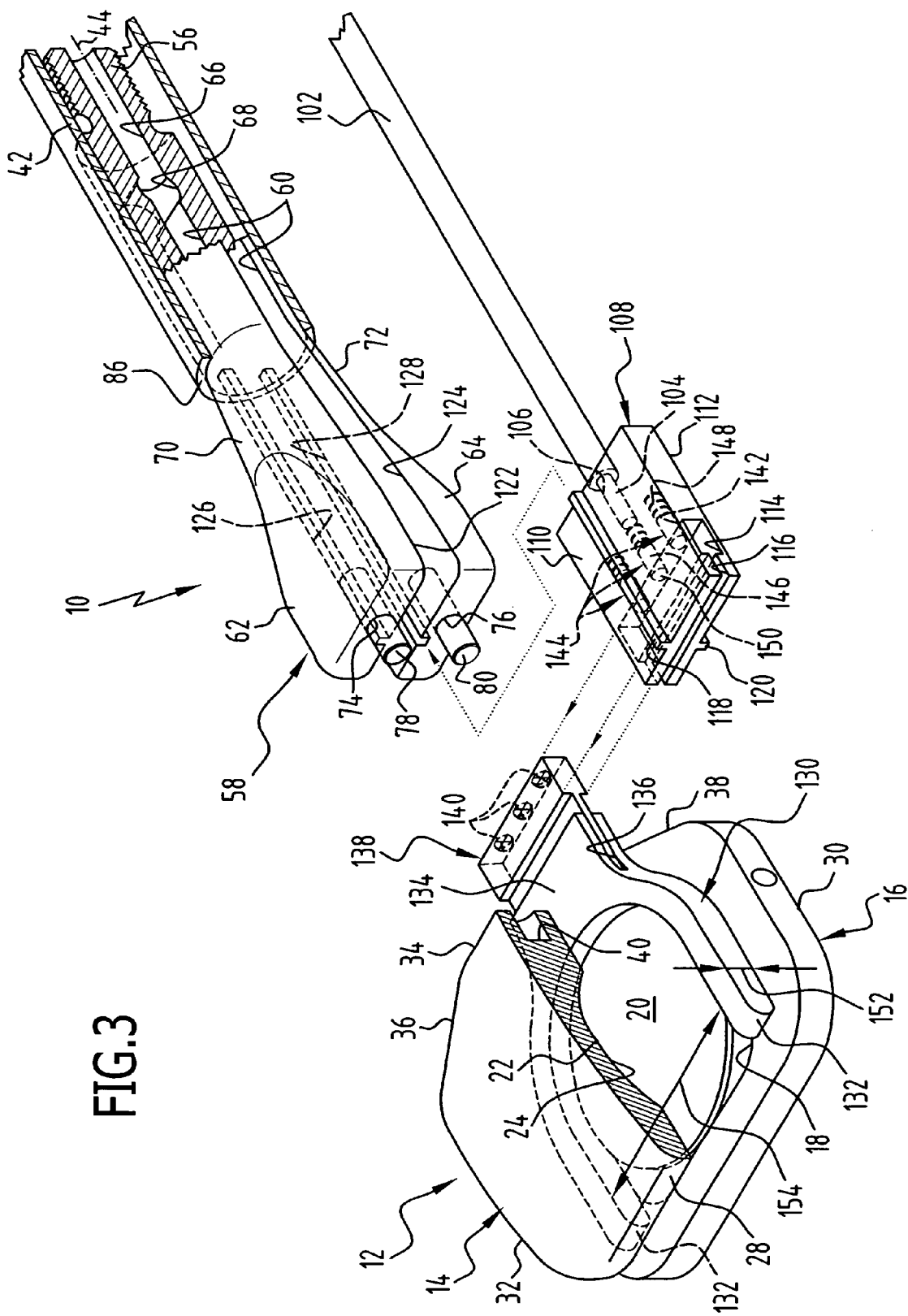
FIG. 3: a perspective, part-sectional and/or partially broken-through view of the instrument of FIG. 1 during connection to an intervertebral implant.

FIG. 1 shows an insertion instrument, which is provided as a whole with the reference character 10 and may be used to insert an intervertebral implant in the form of a replacement intervertebral disk 12 into a non-illustrated intervertebral space between two adjacent vertebral bodies of two vertebrae of a human or animal spinal column.

The replacement intervertebral disk 12 illustrated in FIGS. 1 to 4 comprises a top end plate 14 and a bottom end plate 16, which serve as abutment elements for abutment against the two non-illustrated adjacent vertebral bodies. The bottom end plate 16 is provided with a substantially cuboidal indentation 18, which forms a receiver for a polyethylene core 20 serving as an articulated element. In the described embodiment of the replacement intervertebral disk 12 the polyethylene core 20 is seated immovably in the indentation 18 but might however alternatively be supported in a movable manner. A convexly curved surface of the polyethylene core 20 facing towards the top end plate 14 and forming part of a spherical surface forms an articulated surface 22 for producing an articulated connection between the top end plate 14 and the bottom end plate 16.

The top end plate 14 is provided with a hollow-spherical sliding surface 24 facing towards the bottom end plate 16 and corresponding to the articulated surface 22. This development allows, in accordance with a radius R of the articulated surface 22 and/or of the sliding surface 24, a rotational movement of the top end plate 14 relative to the bottom end plate 16 about a centre of rotation 26.

Each of the two end plates 14 and 16 in plan view has a polygonal shape, namely having in each case a back edge 28, two side edges 30 and 32 extending at right angles to the back edge 28, a short front edge 34 extending parallel to the back edge 28, and two holding edges 36 and 38 connecting the front edge 34 to the side edges 30 and 32 and inclined in each case by 30° relative to the front edge 34. In other variants, angles of 45° would also be conceivable. For detachably connecting the replacement intervertebral disk 12 to the insertion instrument 10, the two side edges 30 and 32, the front edge 34 and the holding edges 36 and 38 of both the top and the bottom end plates 14 and 16 are provided in each case with blind hole bores 40, which project at right angles from the respective edges. The blind hole bores 40 in the top end plate 14 and in the bottom end plate 16 are arranged in the identical edges so as to be aligned in each case parallel and above one another, so that in an insertion position of the replacement intervertebral disk 12 longitudinal axes of the mutually associated blind hold bores 40 in identical edges of both end plates 14 and 16 define in each case one plane.

The insertion instrument 10 comprises an elongate tubular sleeve 42, which defines a longitudinal axis 44 in longitudinal direction of the insertion instrument 10. At the proximal end, the sleeve 42 is connected in a rotationally fixed manner to a rotary sleeve 46, which is provided with an internal thread 48. The sleeve 42 penetrates a shank 50 that is provided with a central longitudinal bore 52. A blind hole bore 54, which at the distal end widens the longitudinal bore 52 in the shank 50, is provided with an internal thread that is connected to an external thread of a threaded bolt 56, which is directed integrally with a holding fork 58 in proximal direction.

The holding fork 58 adjoining the threaded bolt 56 is of a rod-shaped design but is provided along over half of its length at the distal end with a slot 60 for forming a top and a bottom fork end 62 and 64. Both the threaded bolt 56 and the adjoining, non-forked portion of the holding fork 58 are provided with a bore 66 that is a continuation of the longitudinal bore 52. To facilitate a springing of the fork ends 62 and 64, these are provided in the interior adjacent to the non-forked portion of the holding fork 58 with a weakening in the form of an annular groove 68 facing towards the longitudinal axis 44.

The, at the proximal end, substantially cylindrical holding fork 58 widens conically in the direction of its distal end, so that the two fork ends 62 and 64 each have run-on bevels 70 and 72 serving as slide surfaces. The run-on bevels 70 and 72 are adjoined by two substantially cuboidal regions of the fork ends 62 and 64, which are provided in each case symmetrically to one another with at least one blind hole bore 74 and 76 each, which are aligned relative to one another parallel to the longitudinal axis 44 and open in distal direction and into each of which a holding pin 78 and/or 80 serving as an abutment-element holding element is inserted and connected firmly to the respective fork end 62 and/or 64. The holding pins 78 and 80 are so designed that they are introducible into the blind hole bores 40 of the replacement intervertebral disk 12 for detachably connecting the insertion instrument 10 to the replacement intervertebral disk 12.

At the proximal end, the shank 50 is equipped with an annular flange 84 that is provided with an external thread 82, wherein the external thread 82 corresponds to the internal thread 48 of the rotary sleeve 46. This allows the sleeve 42 to be moved in a defined manner relative to the shank 50, wherein by means of the corresponding internal and external threads 48 and 82 a defined rotational/translational movement of the sleeve 42 is preset.

A distal end of the sleeve 42 forms an annular stop 86, which limits an outward rotating movement of the fork ends 62 and 64 away from the longitudinal axis 44. Together with the stop 86, the run-on bevels 70 and 72 provided on the fork ends 62 and 64 therefore form a stop device. The further the sleeve 42 is slid forward in distal direction, the further the two fork ends 62 and 64 are moved towards one another. Conversely, an outward rotating of the fork ends 62 and 64 biased towards one another by the sleeve 42 is made possible when the sleeve 42 is rotated back in proximal direction.

The shank 50 extends at the proximal end beyond the annular flange 84 and is screwed into a handle 88, which is provided with a receiving bore 90 for a proximal end of the shank 50. Transversely of the longitudinal axis 44 the handle 88 is provided with a securing bore 92, into which a threaded pin 94 may be screwed to secure the shank 50 in a rotationally fixed manner on the handle 88. The threaded pin 94 for this purpose engages into a small recess 96 of the shank 50.

On a proximal end of the handle 88 a rotary knob 98 is rotatably supported. The rotary knob 98 forms part of a spindle mechanism and for this purpose is provided with an internally threaded blind hole bore (not illustrated in detail), which is open in distal direction. The rotary knob is used to move a threaded rod 102, which is provided at its proximal end with an external thread corresponding to the internal thread of the rotary knob 98. The threaded rod 102 penetrates a longitudinal bore 100 of the handle 88 that is a continuation of the receiving bore 90 of the shank 50 in proximal direction, and also penetrates the longitudinal bore 52 that penetrates the shank 50 along the entire length thereof. A distal end of the threaded rod 102 is designed with a single-stage taper in the form of an externally threaded bolt 104.

The threaded bolt 104 is screwed into an internally threaded blind hole bore 106 of a cuboidal holding element 108. Adjacent to its distal end the holding element 108 is provided, parallel to top and bottom sides 110 and 112 forming largest lateral faces thereof, with a cuboidal transverse opening 114, which by means of a parallel-running slot 116 is open in distal direction. In other words, the transverse opening 114 and the slot 116 form a groove, which is open in distal direction and widens in a single stage in proximal direction. Disposed on the top side 110 and the bottom side 112 are laterally offset, narrow, cuboidal longitudinal ribs 118 and 120 respectively, which extend parallel to the longitudinal axis 44 and are of a corresponding design to longitudinal grooves 126 and 128, which are formed parallel to the longitudinal axis 44 in mutually opposing inner faces 122 and 124 of the fork ends 62 and 64. They form longitudinal guides for the holding element 108 when it is displaced parallel to the longitudinal axis 44 in distal or proximal direction by rotating the rotary knob 98 on the proximal end of the insertion instrument 10.

A substantially U-shaped stirrup spacing member 130, which comprises two limbs 132 extending in distal direction parallel to the longitudinal axis 44, is connectable to the holding element 108. At the proximal end, the limbs 132 are formed integrally with a holding plate 134, which is provided with a slot 136 extending parallel to a plane defined by the two limbs 132. A plate-shaped end of a cuboidal connection element 138 is inserted into the slot, namely in such a way that the connection element 138 is insertable transversely of the longitudinal axis 44 into the transverse opening 114, wherein the plate-shaped end in said case penetrates the slot 116. The transverse opening 114 and the slot 116 form a transverse guide for the stirrup spacing member 130, so that the stirrup spacing member 130 is displaceable in a defined manner transversely of the longitudinal axis 44.

For securing defined positions of the stirrup spacing member 130 relative to the holding element 108, a wall surface of the connection element 138 facing in proximal direction is provided with three symmetrically arranged, hollow-spherical indentations 140. Alternatively, only two indentations may be provided, wherein one may be hollow-spherical and the other elongate. Provided in the holding element and extending from the transverse opening 114 in proximal direction and parallel to the longitudinal axis 44 are three blind hole bores 142, into which spherical thrust pieces 144 spring-biased in distal direction are inserted. These are formed by a helical spring 148, which is supported at the proximal end against the blind hole bore 142 and at the distal end against a detent element 146, wherein only a hemispherical end 150 may project from the blind hole bore 142 and engage into one of the indentations 140.

The spherical thrust pieces 144 together with the indentations 140 form a securing device for securing the stirrup spacing member 130 in defined transverse movement positions. In principle, it would be conceivable to provide more or fewer than three spherical thrust pieces and/or indentations 140 in order to achieve further defined securing positions. If an indentation is designed in the form of an elongate hole, then a transverse movement position movable in a defined manner may be preset, wherein the spherical thrust pieces may move freely between two defined end stops in the elongate indentation.

The previously described insertion instrument 10 may be used to insert the replacement intervertebral disk 12 into an intervertebral space. For this purpose, first the stirrup spacing member 130 is moved into its most distal position by rotating the rotary knob 98 accordingly. The sleeve 42 is moreover moved into its most proximal position by rotation at the rotary sleeve 46. The insertion instrument 10 is connected to the replacement intervertebral disk 12 by introducing the holding pins 78 and 80 into a blind hole bore 40 of the top and bottom end plate 14 and 16 respectively. The stirrup spacing member 130 is chosen in accordance with the selected replacement intervertebral disk 12. This means that, for larger or smaller replacement intervertebral disks 12, different stirrup spacing members 130 are connectable to the holding element 108. What is crucial in each case is that the limbs 132 of the stirrup spacing member 130 may be supported both against the top end plate 14 and against the bottom end plate 16 while at least partially encompassing the polyethylene core 20. It should further be ensured that the stirrup spacing member 130 is advanced far enough in distal direction to prevent a rotation of the two end plates 14 and 16 with the back edges 28 towards one another.

In a subsequent step, the replacement intervertebral disk 12 may be secured by clamping on the insertion instrument by moving the sleeve 42 in distal direction by rotating the rotary sleeve 46. The stop 86 sliding along on the run-on bevels 70 and 72 forces the two free fork ends 62 and 64 to execute a movement in the direction of the longitudinal axis 44, which leads to a jamming of the holding pins 78 and 80 in the blind hole bores 40. In this way, the replacement intervertebral disk 12 is held securely on the insertion instrument and may be introduced into the intervertebral space. As soon as the replacement intervertebral disk 12 has been implanted in the desired shape, either the stirrup spacing member 130 between the two end plates 14 and 16 may first be withdrawn or a jamming of the holding pins 78 and 80 in the blind hole bores 40 may be cancelled by rotating the sleeve 42 back in proximal direction. The insertion instrument 10 is easily detachable in the described manner from the replacement intervertebral disk 12.

Figure 4:
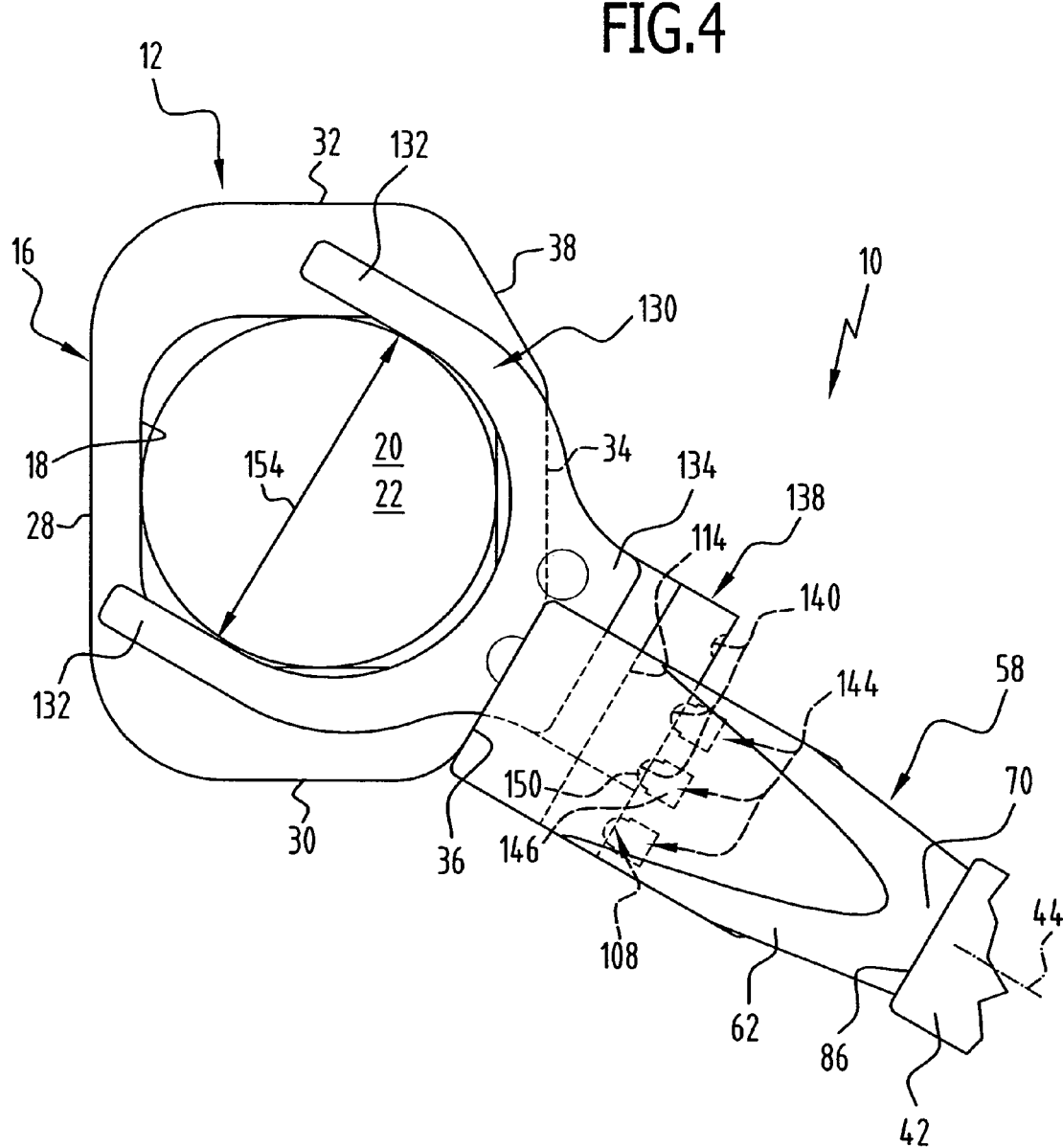
FIG. 4: a plan view of a distal end of the instrument with an intervertebral implant held thereon, in a laterally offset position of the spacer element.

The special development of the connection between the stirrup spacing member 130 and the holding element 108 allows the insertion instrument 10 to be connected to the replacement intervertebral disk 12 also in the manner illustrated in FIG. 4. If the holding pins 78 and 80 are namely introduced into blind hole bores 40 of the holding edges 36 and 38, or alternatively of the front edge 28 or of the side edges 30 or 32, the longitudinal axis 44 no longer always extends symmetrically through the polyethylene core 20. The result of this would be that the stirrup spacing member 130 might not encompass the polyethylene core 20 solely by moving in distal direction. The lateral offset of the longitudinal axis 44 may however be compensated by lateral displacement of the stirrup spacing member 130 relative to the holding element 108. The spherical thrust pieces 144 and the corresponding indentation 140 are disposed in such a way that in a displaced position only two spherical thrust pieces 144 engage into two corresponding indentations 140. If only one spherical thrust piece 144 is provided, then it engages in different transverse movement positions into different indentations 140. The lateral offset of a bisector of the stirrup spacing member 130 from the longitudinal axis 44 therefore corresponds precisely to the distance between two indentations 140.

As already indicated, for replacement intervertebral disks 12 of differing size, stirrup spacing members 130 of differing size are connected to the holding element 108. In said case, a height 152 of the limbs 132 as well as the distance 154 between them may in particular vary extremely from one another in different stirrup spacing members.

The insertion instrument 10 is preferably designed so that it may be completely disassembled for sterilizing purposes, i.e. the sleeve 42 and the threaded rod 102 may be fully detached from the shank 50.

The invention claimed is:

1. A surgical instrument for inserting an intervertebral implant into an intervertebral space between two adjacent vertebral bodies of two vertebrae of a human or animal spinal column, said instrument comprising:
an elongate shank and a spacer element,
said shank defining a longitudinal direction and comprising at least two abutment-element holding elements, each abutment-element holding element having a distal end for detachable connection to a first abutment element and a second abutment element of the intervertebral implant, the distal ends of the abutment-element holding elements being moveable toward one another in a transverse direction that is substantially perpendicular to the longitudinal direction,
said spacer element projecting from the distal end of the shank in extension thereof and which, when the abutment elements are connected to the instrument, engages between the abutment elements and holds them a defined spacing apart from one another, and said spacer element being supported movably relative to at least one of the abutment-element holding elements in a direction substantially parallel to the longitudinal direction of the shank, the spacer element being laterally displaceable relative to the shank in a lateral direction that is substantially perpendicular to the longitudinal direction and substantially perpendicular to the transverse direction.

2. The instrument according to claim 1, wherein said spacer element is of a substantially U-shaped design.

3. The instrument according to claim 1, wherein said spacer element comprises two limbs extending in a distal direction substantially parallel to the longitudinal direction of the shank.

4. The instrument according to claim 1, wherein said spacer element is securable in at least one lateral movement position, which is defined or movable in a defined manner, relative to said shank.

5. The instrument according to claim 1, wherein a displacement guide is provided for the spacer element.

6. The instrument according to claim 5, wherein said displacement guide is formed by an opening, said opening being disposed transversely of the longitudinal direction of said shank and being open at least partially in the direction of the spacer element.

7. The instrument according to claim 1, wherein said spacer element is supported movably on a holding element, said holding element being supported movably relative to said shank in the longitudinal direction thereof.

8. The instrument according to claim 7, wherein at least two corresponding locking elements are provided for locking a relative position of said spacer element and said holding element in a locking position, in which said spacer element and said holding element are secured such as to be immovable relative to one another or movable in a defined manner, said spacer element comprising a first and said holding element comprising a second of said at least two locking elements.

9. The instrument according to claim 8, wherein said first locking element is a locking receiver and said second locking element is a locking projection.

10. The instrument according to claim 9, wherein said locking projection is movably supported substantially parallel to the longitudinal axis of said shank.

11. The instrument according to claim 10, wherein said locking projection is supported spring-biased in the direction of said locking receiver.

12. The instrument according to claim 8, wherein one of said at least two locking elements is designed in the form of a spherical thrust piece.

13. The instrument according to claim 8, wherein either of said holding element or said spacer element comprises at least two locking elements.

14. The instrument according to claim 1, wherein a stop device is provided for limiting a movement of said abutment-element holding elements away from one another.

15. The instrument according to claim 14, wherein said stop device comprises a stop element, said stop element encompassing both abutment-element holding elements in each case at least partially.

16. The instrument according to claim 15, wherein said stop element is formed by an elongate tubular sleeve.

17. The instrument according to claim 16, wherein said stop device comprises at least one slide surface for a distal end of the sleeve, said slide surface being formed on one of said abutment-element holding elements or adjacent thereto on the shank, said slide surface in a distal direction relative to the longitudinal direction of the shank and being inclined away from a longitudinal axis of said shank.

18. The instrument according to claim 1, wherein at least the distal end of said instrument is of a forked design comprising two fork ends, said two fork ends being movable relative to one another and forming or carrying said abutment-element holding elements.

19. The instrument according to claim 1, wherein a mechanical drive unit is provided for moving said spacer element in the longitudinal direction of said shank.

20. The instrument according to claim 19, wherein said mechanical drive unit comprises a threaded spindle extending in the longitudinal direction of the shank and a rotary knob supported on said shank and coupled to said threaded spindle.

21. The instrument according to claim 1, wherein said spacer element is held in a detachably connectable manner on said instrument.

22. An implant system comprising an intervertebral implant for insertion into an intervertebral space between two adjacent vertebral bodies of two vertebrae of a human or animal spinal column as well as an insertion instrument for inserting the intervertebral implant into the intervertebral space, said intervertebral implant comprising a first abutment element for abutment against one of said two adjacent vertebral bodies and a second abutment element directly or indirectly supported in an articulated manner on said first abutment element for abutment against the other of said two adjacent vertebral bodies, said insertion instrument being a surgical instrument according to claim 1.

23. The implant system according to claim 22, wherein said intervertebral implant comprises an articulated element disposed between the first and the second abutment element.

24. The implant system according to claim 23, wherein said articulated element can be encompassed at least partially by the spacer element.

25. The implant system according to claim 23, wherein said articulated element and one of said abutment elements are of an integral construction.

26. The implant system according to claim 23, wherein said articulated element and at least one of said abutment elements are disposed adjacent to one another.

27. The implant system according to claim 23, wherein said articulated element and at least one of the abutment elements are either non-positively or positively connected to one another.

28. The implant system according to claim 22, wherein said spacer element comprises two limbs extending in distal direction substantially parallel to the longitudinal direction of the shank.

29. The implant system according to claim 28, wherein a spacing between the two limbs is greater than a width of said articulated element, said spacing between said two limbs corresponding at most to the width of said first and second abutment element.

30. The implant system according to claim 22, wherein a height of said spacer element is equal to or greater than a minimum possible spacing of said first abutment element from said second abutment element.

31. The implant system according to claim 22, wherein said abutment-element holding element comprises at least one holding pin, said at least one holding pin projecting in a distal direction parallel to the longitudinal direction of said shank and being of a corresponding design to at least one holding-pin receiver of said abutment element.

32. The implant system according to claim 22, wherein said intervertebral implant is a replacement intervertebral disk.

33. A surgical instrument for inserting an intervertebral implant into an intervertebral space between two adjacent vertebral bodies of two vertebrae of a human or animal spinal column, said instrument comprising:
an elongate shank and a spacer element,
said shank defining a longitudinal direction and comprising two abutment-element holding elements, each abutment-element holding element having a distal end, for detachable connection to a first abutment element and a second abutment element of the intervertebral implant, the distal ends of the abutment-element holding elements being moveable toward one another in a transverse direction that is substantially perpendicular to the longitudinal direction,
said spacer element projecting from the distal end of the shank in extension thereof and comprising two limbs extending in a distal direction substantially parallel to the longitudinal direction of the shank, and said spacer element being supported movably relative to the two abutment-element holding elements in a direction substantially parallel to the longitudinal direction of the shank, the spacer element being laterally displaceable relative to the shank in a lateral direction that is substantially perpendicular to the longitudinal direction and substantially perpendicular to the transverse direction.

34. The instrument according to claim 33, wherein said two abutment element holding elements comprise a pair of holding pins to insert an intervertebral implant into an intervertebral space between two adjacent vertebral bodies of two vertebrae of a human or animal spinal column, said intervertebral implant comprising a first abutment element for abutment against one of the two adjacent vertebral bodies and a second abutment element directly or indirectly supported in an articulated manner on said first abutment element for abutment against the other of said two adjacent vertebral bodies.

35. An implant system comprising an intervertebral implant for insertion into an intervertebral space between two adjacent vertebral bodies of two vertebrae of a human or animal spinal column as well as an insertion instrument for inserting the intervertebral implant into the intervertebral space, said intervertebral implant comprising a first abutment element for abutment against one of said two adjacent vertebral bodies and a second abutment element directly or indirectly supported in an articulated manner on said first abutment element for abutment against the other of said two adjacent vertebral bodies, said insertion instrument being a surgical instrument according to claim 33.

* * * * *